United States Patent [19]

Pink et al.

[11] Patent Number: 5,538,714
[45] Date of Patent: Jul. 23, 1996

US005538714A

[54] USE OF POLYVINYL PYRROLIDONE FOR REDUCING THE ADHERENCE OF ORAL BACTERIA

[75] Inventors: Carol S. Pink; Jane L. Smith, both of Hersham; Andrew W. Smith, Beckenham, all of England

[73] Assignee: SmithKline Beecham plc, Brentford, United Kingdom

[21] Appl. No.: 295,640

[22] PCT Filed: Feb. 25, 1993

[86] PCT No.: PCT/GB93/00389

§ 371 Date: Aug. 26, 1994

§ 102(e) Date: Aug. 26, 1994

[87] PCT Pub. No.: WO93/16680

PCT Pub. Date: Sep. 2, 1993

[30] Foreign Application Priority Data

Feb. 29, 1992 [GB] United Kingdom ............... 9204414

[51] Int. Cl.⁶ ................................................. A61K 7/16

[52] U.S. Cl. ................. 424/49; 424/50; 424/54; 424/15; 424/52

[58] Field of Search ................. 424/49, 50, 52, 424/55, 24

[56] References Cited

U.S. PATENT DOCUMENTS 2,783,182  2/1957  Nelson, Jr. .
5,130,124  7/1992  Marianos ............................. 424/53

FOREIGN PATENT DOCUMENTS 1075782   10/1954  France .
2471780    6/1981  France .
WO84/04546 11/1984  WIPO .

*Primary Examiner*—Paul J. Killos
*Attorney, Agent, or Firm*—James M. Kanagy; William T. King; Edward T. Lentz

[57] ABSTRACT

The present invention relates to a method of reducing the adherence of bacteria to tooth surfaces, to compositions for use in such a method and to processes for the preparation thereof.

12 Claims, No Drawings

USE OF POLYVINYL PYRROLIDONE FOR REDUCING THE ADHERENCE OF ORAL BACTERIA

This Application is a 371 of PCT/GB93/00389 25 Feb. 1993.

The present invention relates to a method of reducing the adherence of bacteria to tooth surfaces, to oral hygiene compositions comprising polyvinyl pyrrolidone (PVP) for use in such methods and to processes for the preparing such compositions.

Bacteria present in the oral cavity, as part of the normal microflora thereof, may be deposited in the pellicle formed on the tooth enamel and then be transformed into plaque. This may in turn lead to caries, calculus and periodontal disease. Accordingly methods for reducing the adherence of bacteria to the tooth enamel should be of benefit in oral hygiene as they should be associated with reduced plaque formation. Agents used in such methods are commonly referred to as "anti-adherence" agents. Examples of such already in use include silicone polymers. Anti-adherence agents modify the tooth surfaces, thereby interfering with the normal bacterial absorption mechanisms.

We have now surprisingly found that polyvinyl pyrrolidone (PVP) has anti-adherence properties. Polyvinyl pyrrolidone has previously been included in oral hygiene compositions, at comparatively low levels (typically about 0.1%) as an auxilliary thickening agent and foam enhancer. In addition, PVP has been proposed for use in oral hygiene compositions, in dentifrices as an agent to remove stain, in particular tobacco stain (GB 741 315, Colgate Palmolive-Peet Co), and in conjunction with chlorophyll, to inhibit the formation of stain associated therewith (GB 739 936, Colgate-Palmolive Co). More recently, PVP has also been suggested as an additive for dentifrices packaged in plastics dispensers, to reduce the release of volatile flavour oils therefrom (U.S. Pat. No. 4,590,065, Colgate-Palmolive Co).

Accordingly, the present invention provides a method of reducing or preventing the adherence of oral bacteria to tooth enamel, which method comprises applying an anti-adherence effective amount of polyvinyl pyrrolidone to the oral cavity.

Such a method of treatment has the advantage or reducing or preventing the adherence of oral bacteria to tooth enamel and thereby reducing the amount of subsequent plaque formation.

Polyvinyl pyrrolidone suitable for use in the present invention preferably has an average molecular weight in the range 5,000 to 100,000, more preferably in the range 5,000 to 50,000. Grades of polyvinyl pyrrolidone of average molecular weight 10,000 and 40,000 are available from Sigma Chemical Co whilst a grade with an average molecular weight of 30,000 is available from GAF Corporation.

Polvinyl pyrrolidone for use in the present invention will preferably be presented in an oral hygiene composition further comprising a dentally acceptable excipient or carrier. Polyvinyl pyrrolidone is suitably present in at least 1%, preferably between 2 and 30%, more preferably between 5 and 25%, advantageously between 10 and 25%, by weight of such composition.

Oral hygiene compositions of the present invention may also usefully comprise in an antiplaque agent. Suitable anti-plaque agents include cationic antibacterial agents such as the bis-biguanides chlorhexidine and alexidine and orally acceptable salts thereof and quaternary ammonium compounds such as cetyl pyridinium chloride and also nonactionic antibacterial agents such as triclosan, bromochlorophene and hexachlorophene. Suitably, the antiplaque agent is incorporated at from 0.001 to 10%, preferably from 0.01 to 5% by weight of the composition.

Oral hygiene compositions according to the present invention may also usefully comprise a fluoride ion source, to provide an anti-caries activity. Suitable fluoride ion sources include metal fluoride salts, for instance alkali metal fluoride salts such as sodium fluoride, amine fluoride salts, alkali metal monofluorophosphate salts such as sodium monofluorophosphate and amine monofluorophosphate salts. Suitably the fluoride ion source may, if present, provide from 50 to 3500 ppm, preferably 100 to 2500 ppm of fluoride ions.

Orally hygiene compositions of the present invention maybe provided in any of the presentations normally used for such products, for instance, dentifrices including toothpastes and toothpowders, abrasive and nonabrasive gels, mouthwashes, gargles, irrigating solution, mouthsprays and presentations for sucking or chewing by the user such as gums, pastilles and lozenges. Components for the orally acceptable carder or excipient will be selected according to the particular type of presentation involved.

Preferably the composition will be provided as a mouthwash or gargle, for use either before or, more preferably, after the use of another oral hygiene composition, for instance a conventional toothpaste.

For a mouthwash composition, the dentally acceptable excipient or carrier will generally have an aqueous or aqueous ethanol base. The composition may further comprise a surfactant and humectant, to enhance the aesthetic and cosmetic qualities of the composition. If the composition is presented as dentifrice, the dentally acceptable excipient or carrier will generally comprise a liquid vehicle including water and a humectant, a surfactant, a thickening agent, and a solid vehicle including an abrasive.

Suitable surfactants include anionic, nonionic, cationic and amphoteric surfactants, and mixtures thereof.

Suitable anionic surfactants include the water-soluble salts of higher fatty acid monoglyceride monosulphates, for example, sodium hydrogenated coconut fatty acid monoglyceride monsulphate; higher alkylsulphates, for example, sodium laurylsulphate; alkylarylsulphonates, for example, sodium dodecylbenzene sulphonates; and higher alkyl sulphoacetates, for example, sodium laurosulphate. There may also be used the saturated higher aliphatic acyl amides of lower aliphatic amino carboxylic acids having 12 to 16 carbon atoms in the acyl radial and in which the amino acid portion is derived from the lower aliphatic saturated mono-amino carboxylic acids having 2 to 6 carbon atoms, such as the fatty acids of glycine, sarcosine, alanine, 3-amino propanoic acid and valine, in particular the N-lauroyl, myristoyl and palmitoyl sarcosinate compounds. Other suitable anionic surfactants include low anionic surfactants such as sodium N-methyl-N-cocoyl laurate, marketed under the trade name ADINOL by Croda Chemical Co.

Suitable nonionic surfactants include, for example, polyethoxylated sorbitol esters, in particular polyethoxylated sorbitol monoesters, for instance, PEG(40) sorbitan di isostearate, and the products marketed under the trade name TWEEN by ICI; polycondensates of ethylene oxide and propylene oxide (poloxamers), for instance, the products marketed under the trade name PLURONIC by BASF-Wyandotte; condensates of propylene glycol; polyethoxylated hydrogenated castor oil, for instance, cremophors; and sorbitan fatty esters.

Suitable amphoteric surfactants include, for example, long chain imidazoline derivatives such as the product marketed under the trade name MIRANOL C2M by Miranol; long chain alkyl betaines, such as the product marketed under the trade name EMPIGEN BB by Albright+Wilson, and long chain alkyl amidoalkyl betaines, such as cocoamidopropylbetaine, and mixtures thereof.

Suitable cationic surfactants include the D,L-2-pyrrolidone-5-carboxylic acid salt of ethyl-N-cocoyl-L-arginate, marketed under the trade name CAE by Ajinomoto Co. Inc., cocoamidopropyl PG dimonium chloride phosphate, available under the trade name MONAQUAT PTC from Mona Corpn., and lauramidopropyl PG dimonium chloride phosphate, available under the trade name MONAQUAT PTL from Mona Corpn.

Advantageously, the surfactant is present in the range 0.005 to 20%, preferably 0.1 to 10%, more preferably 0.1 to 5% by weight of the composition.

Suitable thickening agents include, for instance, nonionic thickening agents such as, for example, $(C_{1-6})$-alkylcellulose ethers, for instance methylcellulose; hydroxy$(C_{1-6})$-alkylcellulose ethers, for instance hydroxypropylcellulose; $(C_{2-6})$-alkylene oxide modified $(C_{1-6})$-alkylcellulose ethers, for instance hydroxypropyl methylcellulose; and mixtures thereof. Other suitable thickening agents include natural and synthetic gums or gum-like material such as Irish Moss, gum tragacanth, sodium carboxymethylcellulose, starch and inorganic thickening agents such as silica and laponite. Advantageously the thickening agent is present in the range 0.01 to 30%, preferably 0.1 to 15%, more preferbly 1 to 5%, by weight of the composition.

Suitable humectants for use in compositions of the invention include for instance, glycerine, sorbitol, propylene glycol or polyethylene glycol, or mixtures thereof; which humectant may be present in the range from 5 to 70%, preferably 5 to 30%, more preferably 10 to 30% by weight of the dentifrice. Suitably, when the nonionic thickening agent is hydroxypropyl methylcellulose, the humectant is present in up to 30% by weight of the dentifrice.

Suitable abrasives for use in dentifrice compositions of the present invention include calcium carbonate, calcium phosphates, calcium pyrophosphate, insoluble sodium metaphosphate, sodium aluminosilicate, alumina, hydrated alumina, zinc orthophosphate, plastics particles and silica, of which silica is preferred.

Suitable silicas include natural amorphous silicas, for instance, diatomaceous earth and synthetic amorphous silicas, for instance, precipitated silicas and silica gels such as silica xerogels. Suitable silica xerogels are described in U.S. Pat. No, 3,538,230. Suitable grades of precipitated silicas have BET surface areas in the range 20 to 300, preferably 20 to 100 m$^2$/g and median agglomerate sizes in the range 2 to 50, preferably 5 to 30μ. Suitable precipitated silicas and silica xerogels are those marketed by Degussa under the trade name SIDENT and by W. R. Grace Corporation, Davison Chemical Division, under the trade name SYLOBLANC, respectively. Suitable silicas also include "low anion" silicas. As used herein, the term "low-anion" silica refers to those in which anionic impurities such as sodium sulphate and sodium silicate which normally arise during the course of the manufacturing process are kept to a minium, through careful control of the manufacturing process. "Low anion" silicas suitably have less than 1%, preferably less than 0.5% advantageously less than 0.25% by weight of anionic impurities. Suitable such "low anion" silicas are described in EP 0 368 130 (Proctor & Gamble), EP 0 315 503 and EP 0 396 459 (Rhone-Poulenc) and WO 90/05113 (J. M. Huber Corp). Alternatively, grades of commercially available silica with anionic impurities may be rendered suitable by washing with deionised water. Conductivity measurements on the water after washing may be used to monitor the efficacy of such washing. Suitably the conductivity of the water after washing is reduced to less than 200 mSiemens/cm. Suitable "low anion" silicas include the grade RP93 available from Rhone-Poulenc.

Suitably, the abrasive will, when present, be so in the range from 5 to 80%, preferably from 10 to 60%, by weight of the composition.

The orally acceptable excipient or carrier may also comprise further optional ingredients such as flavouring agents, sweetening agents, for example, sodium saccharin, dyes, whitening agents, for example, titanium dioxide and preservatives.

Compositions according to the invention will have a pH which is orally acceptable. Suitably, the pH is in the range 4 to 9.5, preferably in the range 5.5 to 8.0.

Compositions according to the invention may be prepared by conventional processes comprising admixing the ingredients together in the appropriate relative amounts in any order that is convenient and finally and if necessary adjusting the pH to the desired value.

It will be appreciated that such use of polyvinyl pyrrolidone as an anti-adherence agent may be advantageously carried out as part of overall regime of oral hygiene which also includes the use of other oral hygiene compositions. Suitable such other compositions include dentifrices containing an abrasive for cleansing the teeth, to remove existing plaque mechanically and further comprising other agents of use in oral hygiene, for instance, an anticaries, antiplaque, antisensitivity or anticalculus agent.

A composition according to the invention comprising polyvinyl pyrrolidone as an anti-adherence agent may be usefully used separately from, or simultaneously with, another oral hygiene composition. Separate use in conjunction with a dentifrice is however preferred, to provide a "pre-" or "post-" brush composition. Separate use, after the use of a dentifrice, is preferred. Anti-adherence compositions of the present invention may therefore be provided as part of an oral hygiene kit further comprising a dentifrice.

The invention will now be illustrated by reference to the following examples.

EXAMPLE 1

Mouthwash

| | |
|---|---|
| Polyvinyl pyrrolidone (av. mol. wt. 30,000) | 20% |
| Sodium Fluoride | 0.05 |
| Ethanol | 10 |
| Flavour | 0.1 |
| Cremaphor RH60 | 0.2 |
| Colour | 0.01 |
| Water (deionised) | qs |

EXAMPLE 2

Biological Data—Evaluation in vitro of
Anti-Adherence Properties of Polyvinyl Pyrrolidone The adherence of the representative bacterial strain *Streptococcus sanguis* to saliva-coated silica beads was evaluated using a radio-labelled technique. The radio-labels are used to assess any effect on bacterial adherence caused by treatment with the putative antiadherence agent.

*S. sanguis* was grown on a blood agar plate for 24 h at 37° C. Brain heart infusion broth containing 3H-thymidine (24 mCi) was inoculated with *S. sanguis* and incubated for 24 h at 37° C. Organisms were harvested by centrifugation at 2000 rpm for 15 min. The supernate was removed and the cells washed (3×) with phosphate buffered saliva (PBS) (18 ml). The cells were finally suspended in PBS (18 ml) to give a suspension containing about $4.25 \times 10^8$ bacterial cells.

Whole unstimulated saliva was collected from at least 15 adult donors and pooled. Debris was removed by centrigation (3000 rpm, 10 min). The resulting supernate was passed through a Buchner funnel containing GF/F filter paper (Whattmann) and sterilised using a 0.45 m filter. This treated saliva was distributed into sterile bijous and frozen until use.

Treated saliva (1 ml) was added to silica beads (20 mg, FLOROSIL) and left for 24 h at 37° C. The excess saliva was removed and the beads washed with PBS (5 ml) to give saliva-coated silica beads.

Bacterial adherence was determined as followed: bacterial suspension (0.2 ml) was added to a plain vial to assess the number of bacteria in the initial broth. To facilitate the release of radioactivity from within the bacterial cells, tissue solubiliser (optisolv.) was added (1 ml per 0.2 ml bacterial suspension). Scintillant (10 ml, Highsafe II) was added and the radioactivity determined by liquid scintillation counting. Further bacterial suspension (1.6 ml) was added to a plain vial to assess the proportion of bacteria from the initial suspension adhering to the glass wall of the vial. Further bacterial suspension (1.6 ml) was added to saliva-coated silica (20 mg) contained in a plain vial to assess the proportion of bacteria adhering to the saliva-coated silica from the initial suspension.

To determine the antiadherence properties of the potential antiadherence agent, a solution of the specified agent (1 ml) was added to the washed saliva-coated beads, left for 2 min and excess then removed. The beads were washed with PBS (2×, 5 ml) and then tested as above: Normal saliva-coated silica beads were included as a control, from which the change in adherence was calculated.

The following results were obtained:

| PVP average molecular wt. | % w/v | % decrease in adherence |
| --- | --- | --- |
| 10000 | 15 | 83 |
| 30000 | 15 | 87 |
| 40000 | 15 | 68 |

The results show that the inclusion of PVP of average molecular weight 10,000, 30,000 or 40,000, at 15% by weight of the composition, gives an anti-adherence effect.

We claim:

1. A method of reducing or preventing the adherence of oral bacteria to tooth enamel which method comprises applying to the tooth enamel a composition containing an antiadherence effective amount of an antiadherent agent which consists essentially of polyvinyl pyrrolidone to a patient in need thereof.

2. The method as claimed in claim 1 in which the polyvinyl pyrrolidone has an average molecular weight in the range 5,000 to 100,000.

3. The method as claimed in claim 2 in which the polyvinyl pyrrolidone has an average molecular weight in the range 10,000 to 40,000.

4. The method as claimed in claim 1 in which polyvinyl pyrrolidone is present in at least 1% by weight of the composition.

5. The method as claimed in claim 4 in which polyvinyl pyrrolidone is present in between 2 and 30% by weight of the composition.

6. The method as claimed in claim 5 in which polyvinyl pyrrolidone is present in between 5 and 25% by weight of the composition.

7. The method as claimed in claim 1 in which the composition is a dentifrice further comprising an abrasive.

8. The method as claimed in claim 1 in which the composition is a mouthwash.

9. The method as claimed in claim 1 in which the composition further comprises a fluoride ion source.

10. The method as claimed in claim 1 in which the composition further comprises an anti-plaque agent.

11. A method as claimed in claim 1 which comprises the further step of using the composition comprising the antiadherent agent after the use of a dentifrice, as a post-brush composition.

12. A method for reducing or preventing the adherence of oral bacteria to tooth enamel in a patient in need thereof, which method comprises applying to the tooth enamel of said patient, a composition containing an anti-adherent/anti-plaque effective amount of polyvinyl pyrrolidone as the sole antiadherent/anti-plaque agent.

* * * * *